US00PP20997P3

(12) United States Plant Patent
Moon

(10) Patent No.: US PP20,997 P3
(45) Date of Patent: May 18, 2010

(54) HOLLY TREE NAMED 'IABOF'

(50) Latin Name: *Ilex×attenuate*
Varietal Denomination: IABOF

(75) Inventor: Dwayne C. Moon, Loganville, GA (US)

(73) Assignee: Southern Selections, LLC, Loganville, GA (US)

( * ) Notice: Subject to any disclaimer, the term of this patent is extended or adjusted under 35 U.S.C. 154(b) by 0 days.

(21) Appl. No.: 12/157,583

(22) Filed: Jun. 11, 2008

(65) Prior Publication Data

US 2009/0313734 P1 Dec. 17, 2009

(51) Int. Cl.
*A01H 5/00* (2006.01)

(52) U.S. Cl. ..... Plt./247

(58) Field of Classification Search ..... Plt./247
See application file for complete search history.

*Primary Examiner*—Annette H. Para
*Assistant Examiner*—Louanne C Krawczewicz Myers
(74) *Attorney, Agent, or Firm*—Polster Lieder Woodruff & Lucchesi, L.C.

(57) ABSTRACT

A holly tree (*Ilex attenuata*) named 'IABOF' having a compact, dense canopy, an increased caliper to height ratio, reduced berry weight load and also capable of being reproduced reliably from vegetative cuttings.

4 Drawing Sheets

Latin name of the genus and species: *Ilex×attenuate.*

Varietal denomination: Holly tree which I have named 'IABOF'.

BACKGROUND OF THE INVENTION

The present invention relates to a new and distinct variety of a holly tree (*Ilex×attenuate*), which I have named 'IABOF'.

Discovery:

I discovered my new tree in the summer of 2002 growing in a production field in Belleview, Fla. among a group of cultivated East Palatka holly trees. These trees were grown from 3 gallon liners purchased in the spring of 2001 from a nursery in Florida. In the summer of 2002, these liners were stepped up into larger containers and relocated to a production field. It was here that I discovered the claimed cultivar 'IABOF.' Evaluation of this tree continued in this field until it was relocated to an observation area Tifton, Ga. in 2006.

Propagation:

'IABOF' was asexually propagated by the method of vegetative cutting in the summer of 2003 in Belleville, Fla. using four inch long cuttings quick dipped in 2500 Indole-3-butyric acid and 1250 1-naphthaleneacetic acid without wounding. This propagation from semi-hardwood cuttings in a peat-perlite media took approximately 10 weeks to complete. Resulting progeny has proven the characteristics of my new variety to be genetically stable. Furthermore, these observations have confirmed that my new variety represents a new and improved variety of holly tree as particularly evidenced by a shorter internode length which develops a more compact, dense canopy, an increased caliper to height ratio, and reduced berry weight load.

Uniqueness:

'IABOF' was discovered in a block of seedling East Palatka holly trees purchased by a nursery from a supplier of liners in Florida. I claim that the genetic characteristics of this tree are the result of naturally occurring cross-pollination. Due to the nature of the liner purchase, the exact source of the mutation is not known. These improved characteristics distinguish my new trees from other typical East Palatka holly trees. At the time this tree was selected, I observed the 'IABOF' holly tree as a darker green, compact growing holly tree having a heavy caliper, reduced fruiting weight load, and tight internode spacing. The remaining trees in this block were typical of the species with irregular structure, branches drooping from berry weight, and signs of Sphaeropsis knot susceptibility. I claim that my 'IABOF' exhibits improved structural and aesthetic qualities in comparison to traditional East Palatka holly trees.

Use:

'IABOF' was observed for a period of several years and is believed to be particularly useful for street tree planting and in large areas such as, but not limited to, golf courses, commercial sites and parks. 'IABOF' will also benefit growers who will profit from a consistent growing tree having a compact form and reduced weight load damage resulting from berry production.

SUMMARY OF THE INVENTION

Background:

An East Palatka holly tree, which was discovered as a hybrid in East Palatka, Fla. in the 1920's, is typically pyramidal-shaped in youth and develops an upright oval canopy at maturity. The East Palatka holly tree is native to central Florida. It thrives well in the heat and humidity of the southeastern United States. East Palatka holly trees prefer moist, well-drained soils in these areas, but adapts readily to harsh conditions such as poor drainage, compacted soils, and drought. My new cultivar differs from the species in that it is more compact in height and width, heavier in caliper to height ratio, has shorter internode length and is less susceptible to branch damage due to reduced weight of berries. I expect my new variety 'IABOF' to perform as well as the species.

Industry representation:

A cultivated East Palatka holly tree is represented in the industry by materials reproduced by vegetative cuttings from multiple sources. This accounts for a degree of variability in growth rate and habit both in the landscape industry and nursery industry. East Palatka holly trees are widely used in the coastal southeastern United States as an evergreen screen and specimen accent tree. At the time of this submittal, there is no cultivar selection of East Palatka holly tree that I am aware of in the nursery industry. The dark foliage color, reduced berry load, compact pyramidal form and increased caliper make my selection unique.

DESCRIPTION OF THE DRAWINGS

The accompanying photographs depict the color and foliage of my new variety

East Palatka holly tree as nearly as is reasonably possible to make the same in a color illustration of this character.

DETAILED DESCRIPTION

Figure 1:
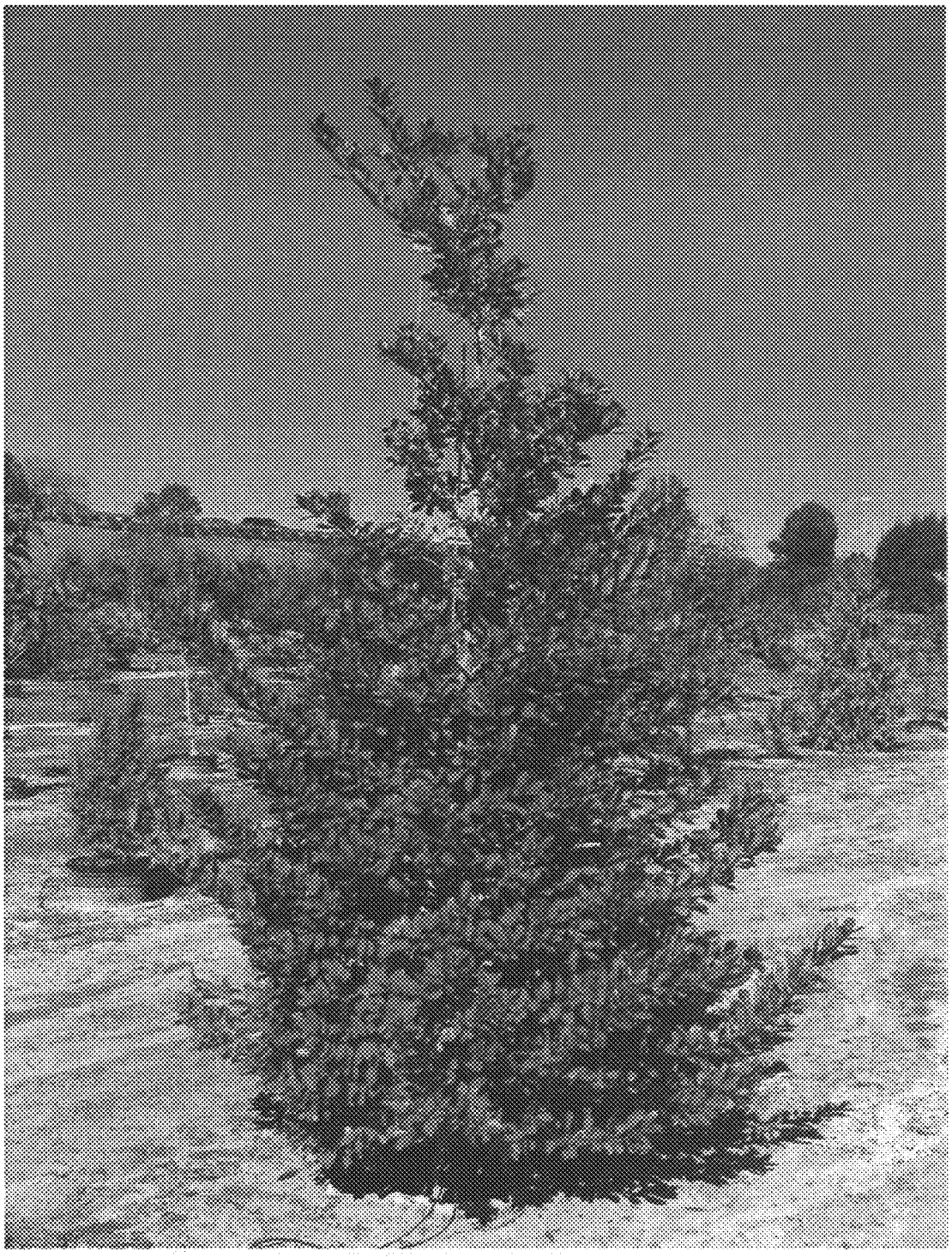
FIG. 1, taken in Tifton, Ga. in 2006, shows the transplanted holly tree at 5 years old, 6.5 feet high, 3.0 feet wide and 2.0 inches in caliper. This photo depicts pyramidal habit with dense branching.
Figure 2:
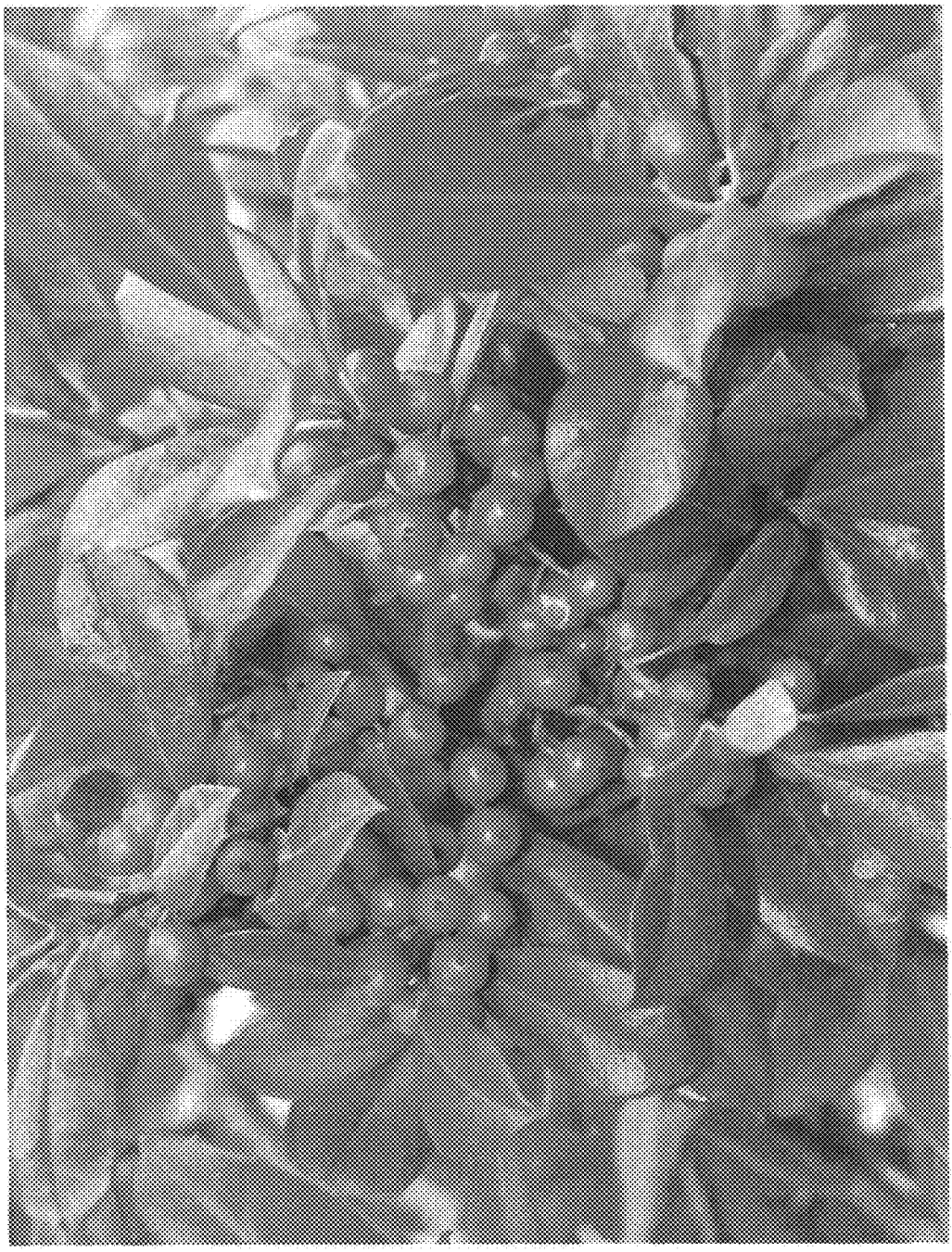
FIG. 2, taken in Tifton, Ga. in Late summer of 2006, shows the foliage and fruit of my new variety of holly tree.
Figure 3:
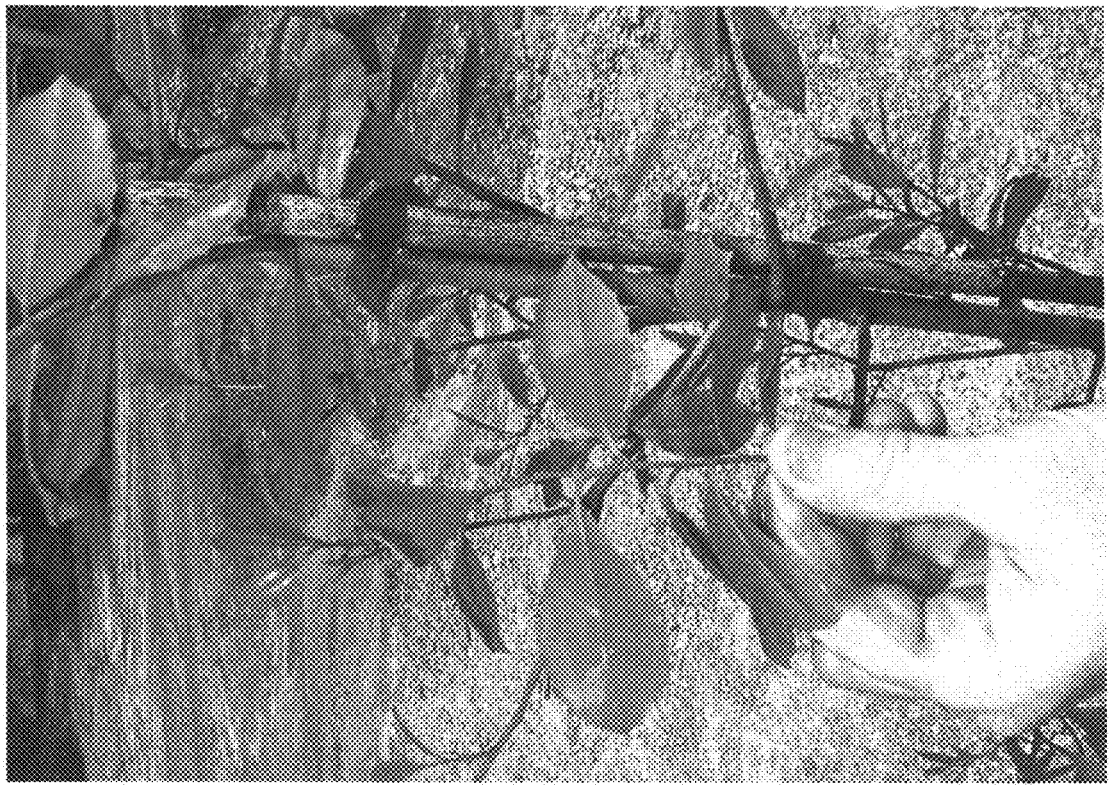
FIG. 3 shows the lower leaf surface of my new variety of holly tree.
Figure 4:
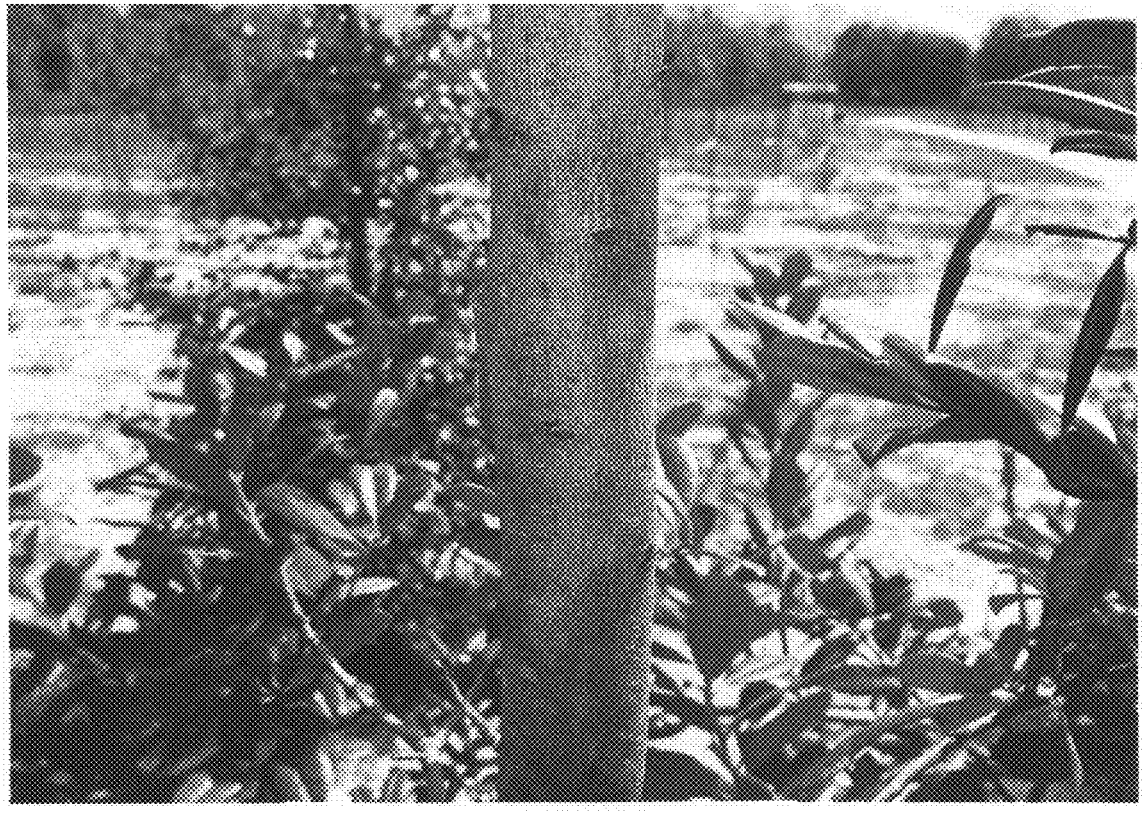
FIG. 4 shows the trunk of my new variety of holly tree.

Botanical description of the plant:

The following is a detailed description of the 'IABOF' holly tree with color terminology in accordance with The Royal Horticulture Society (R.H.S.) color chart except where the context indicates a term having its plain and ordinary meaning.

My new tree has not been observed under all growing conditions and variations may occur as a result of different growing conditions. All progeny of my new variety, insofar as have been observed, have remained genetically stable in all characteristics described hereinafter. Other than as set out hereinafter, as of this time, no other characteristics have been observed by the inventor are different from that of common East Palatka holly trees.

Parentage: Seedling of East Palatka holly trees grown from container liner purchased in 2001 from a nursery in Florida.

Locality where grown and observed: 'IABOF' holly trees are currently in production at a nursery in Belleview, Marion County, Fla. This area of Marion County has a sandy loam soil type with rainfall that varies between 30 inches and 60 inches annually. This particular area is located in USDA Hardiness Zone 9.

Size and growth rate: The original tree, aged 5 years measured 2.0 inches in caliper at 6.0 inches above the ground. The height of 6.5 feet and spread of 3.0 feet provides a 2.17 height to width ratio. Prior to my 'IABOF' holly tree being transplanted to the observation area, the average growth rate was 1.25 feet in height per year.

Foliage: Alternate, simple, ovate-rounded. The leaf margin is entire with a terminal spine, cuspidate tip and cuneate base. Entire dimension: 1.25 inches wide by 2.5 inches long. Upper surface is smooth, waxy with medium green like (RHS 137C). The underside is smooth, waxy and yellow green like (RHS 144B). The leaf venation type is pinnate. The midrib vein color is yellow green like (RHS 144C). The lateral vein color is yellow like (RHS 146C). The internode length is 0.33 inches. The observed spine is a single terminal spine that is 0.10 inches long and yellow green like (RHS 144B).

Petiole: ⅜ inch long with channeled texture on upper surface and orange red like (RHS 31C) and diameter is 0.07 inches.

Stem: 1 year wood is yellow green like (RHS 145B) and has pubescence. The 2–5 year old stems are striped greyed green like (RHS 197B) in conjunction with wood that is greyed white line (RHS 156A). The lenticels average between 25 to 30 per diameter linear inch stem and are oval shaped with a greyed green line color (RHS 196B).

Flowers: Early to mid May without fragrance. The flower cluster size is ¼ inch wide and 1/10 inch high with 4 oblong petals that have rounded tips that are green white like (RHS 157D) on the tips fading to grayed-orange like (RHS 166D) toward the interior on the upper petal surfaces. The flowers are staminate in cymes.

Buds: Flower buds are ovate, 1/12 inch long and wide and angled at 30–45 degrees and upright color that is green like (RHS 138B).

Fruit: Occurs in tight clusters with the individual berry having a ⅕ inch to ¼ inch diameter and are glossy red like (RHS 43A). Fruit appears in late November to mid December. The clusters of berries vary in quantity from 12 to 18 berries per cluster on average. These clusters measure from 1 to 1.5 inches across and persist from late fall through mid winter depending on weather conditions and animal activity.

Trunk: Smooth, gray, becoming gray-brown like (RHS 201B). At time of submittal, the trunk diameter was 2.0 inches measured 6.0 inches above the ground.

Branching: Slightly ascending to nearly horizontal at the base, emerging at 80–90 degrees from the trunk. Upper branches are more ascending, emerging at 30 degrees or more from the trunk. Color is gray (RHS 195B), becoming gray-brown with age.

Shape: Broad pyramidal with dense branching and dominant central leader.

Root System: Fibrous

Vigor: In production, the progeny have averaged 1.25 feet of vertical new growth per year. The root development from time of softwood cuttings to a finished rooted 3.5 inch pot is five to seven weeks.

Disease: Less susceptible to Sphaeropsis.

Pests: Susceptible to spittlebug.

What is claimed is:

1. A new and distinct holly tree named 'IABOF' substantially as herein shown, illustrated and described, characterized particularly as to novelty by its shorter internode length which develops a more compact, dense canopy, an increased caliper to height ratio and reduced berry weight load.

* * * * *